United States Patent [19]

Schulz et al.

[11] 4,324,590

[45] Apr. 13, 1982

[54] FIXATIVES FOR DENTISTRY AND THEIR USE

[75] Inventors: Hans H. Schulz, Leichlingen; Walter Uerdingen, Berg.Gladbach; Kuno Wagner, Leverkusen, all of Fed. Rep. of Germany

[73] Assignee: Bayer Aktiengesellschaft, Leverkusen, Fed. Rep. of Germany

[21] Appl. No.: 867,210

[22] Filed: Jan. 5, 1978

[30] Foreign Application Priority Data

Jan. 29, 1977 [DE] Fed. Rep. of Germany ....... 2703709

[51] Int. Cl.³ .............................................. C09K 3/00
[52] U.S. Cl. ..................................................... 106/35
[58] Field of Search ................................ 106/35, 252; 260/77.5 A, 77.5 MA; 252/188, 181.3; 428/44, 55, 58, 80

[56] References Cited

U.S. PATENT DOCUMENTS

| | | | |
|---|---|---|---|
| 3,027,399 | 3/1962 | Merten et al. | 260/77.5 A |
| 3,098,755 | 7/1963 | Barth et al. | 428/425 |
| 3,425,973 | 2/1969 | Shaw | 260/77.5 MA |
| 3,728,138 | 4/1973 | Kuehn | 260/77.5 A |

*Primary Examiner*—Theodore Morris
*Attorney, Agent, or Firm*—Sprung, Felfe, Horn, Lynch & Kramer

[57] ABSTRACT

The present invention provides a two-component composition for use to form a solvent-free fixing material suitable for use in dentistry, which fixing material is liquid at room temperature and has a viscosity in the range of from 5,000 to 100,000 cP, said compositions having: a first component comprising at least one organic polyisocyanate with aliphatically and/or cycloaliphatically bonded isocyanate groups; and a second component comprising (a) at least one polyhydroxy compound having a molecular weight in the range of from 200 to 20,000, being substantially free of ether groups, and having at least 2 aliphatically bonded OH groups and (b) from 1 to 60% by weight, relative to the total mixture, of monohydric and/or polyhydric alcohols with a molecular weight below 200 and/or from 0 to 40% by weight, relative to the total mixture, of oligomeric polyesters containing at least 2 OH groups or ester-diols, with an average molecular weight of from 100 to 500, the first and second components of the mixture being present in amounts corresponding to a NCO-/OH ratio of from 0.8:1 1.2:1.

8 Claims, No Drawings

FIXATIVES FOR DENTISTRY AND THEIR USE

The present invention relates to solvent-free fixing materials for dentistry, which are liquid at room temperature and have a viscosity in the range from 5,000 to 100,000 cP. In dentistry, the known dental cements are used as fixing materials and, in addition, as filling materials or subfillings, for fixing crowns and bridges or fixed corrective devices and for filling root canals after root treatment.

In addition to zinc phosphate cements, cements of zinc oxide or magnesium oxide and polymeric acrylate resins have previously been employed for these purposes (DT-AS (German Published Specification) No. 1,617,688).

The phosphate cements are prepared immediately before use by mixing together a zinc oxide powder and phosphoric acid or a buffered concentrated orthophosphoric acid solution. The disadvantage of these known zinc phosphate cements is that the cement itself is strongly acidic and as a result of this can damage the pulp when it is applied immediately to freshly cut dentine. Attempts have therefore already been made to improve dental sealing compositions and dental cements by adding organic polymeric substances or by polymerising, in situ, monomers having an activated double bond. Thus it is stated in German Patent Specification No. 966,278 that polymers should be added to self-hardening compositions based on zinc oxide and phosphoric acid. Making use of monomers which are polymerised in situ should also be avoided in dental cements because of the danger of damage to the pulp.

DT-AS (German Published Specification) No. 1,617,688 also discloses the use of aqueous polymers, combined with zinc oxide, for the preparation of dental cements. In particular a 40% strength aqueous solution of a polyacrylic acid, have a particular molecular weight, combined with zinc oxide is known to be suitable for the preparation of dental cements which adhere well.

In most cases, salt formation to produce zinc polyphosphates or to give zinc salts of polymers containing carboxyl groups leads to hard and fragile dental filling compositions, which can become brittle and can be crushed when exposed to mastication and under the action of hydrolysing conditions. If known organic polymers are to be employed for the preparation of permanently elastic dental filling compositions which are resistant towards hydrolysis, it is possible to prepare homogeneous polymers only when the polymerisation is carried out in situ, using monomers. However, the absorption problems, already described hereinbefore, in the pulp and in the connecting canals to the pulp will then occur.

It has now been found that permanently elastic organic polymers which are resistant towards hydrolysis and have excellent adhesion to dental materials can be obtained when solvent-free two-component fixing materials based on polyisocyanates, such as, for example polyurethane are employed. Polyisocyanates which can be employed are preferably adducts, of low monomer content, with a viscosity of from 1,000 to 50,000 cP, of aliphatic and/or aromatic diisocyanates or triisocyanates.

For this field of application, low-viscosity solvent-free polyhydroxy compounds are particularly suitable reactants for use with the polyisocyanates.

The present invention provides a two-component composition for use to form a solvent-free fixing material suitable for use in dentistry, which fixing material is liquid at room temperature and has a viscosity in the range of from 5,000 to 100,000 cP, said compositions having: a first component comprising at least one organic polyisocyante with aliphatically and/or cycloaliphatically bonded isocyanate groups; and a second component comprising (a) at least one polyhydroxy compound having a molecular weight in the range of from 200 to 20,000, being substantially free of ether groups, and having at least 2 aliphatically bonded OH groups and (b) from 1 to 60% by weight, relative to the total mixture, of monohydric and/or polyhydric alcohols with a molecular weight below 200 and/or from 0 to 40% by weight, relative to the total mixture, of oligomeric polyesters containing at least 2 OH groups or ester-diols, with an average molecular weight of from 100 to 500, the first and second components of the mixture being present in amounts corresponding to a NCO-/OH ratio of from 0.8:1 1.2:1.

The solvent-free fixing materials prepared with the compositions mentioned preferably have a viscosity of from 5,000 to 100,000 cP. In the preparation of unadulterated fixing material from the composition by admixture of the two-components thereof, the viscosities of the resulting mixtures and of the final ready-to-use coating material are, or course, identical, whilst in the preparation of fixing materials, wherein pigments and/or fillers are incorporated into fixing materials prior to use thereof, the viscosities must be chosen so that the viscosity of the resulting ready-to-use (pigment or filler containing) fixing material does not exceed an upper limiting value of 100,000 cP.

Preferred compositions according to the invention are two-component systems, that is to say mixtures of polyisocyanates and hydroxy compounds, wherein the NCO/OH ratio is 1:1. The required viscosity of the ready-to-use mixtures may be readily adjusted by suitable choice of the starting components.

Suitable polyisocyanates for the first component are, for example, hexamethylene diisocyanate, 1-methyl-2,4-diisocyanate-cyclohexane or 1-methyl-2,6-diisocyanato-cyclohexane or mixtures of these isomers, diisocyanto-cyclohexanes or 3,3,5-trimethyl-5-isocyanato-methyl-cyclohexyl isocyanate. Preferably, the isocyanate component has a maximum viscosity of 50,000 cP/20° C. This latter pre-requisite is fulfilled, in particular, by derivatives of hexamethylene diisocyanate, namely tris-(isocyanato-hexyl)-biuret, optionally mixed with its higher homologues. The biuretisation of hexamethyl diisocyanate can be achieved, for example, by reaction with water or tert-butanol in a molar ratio diisocyanate: water or tert. butanol of at least 3:1.

The polyhydroxy compounds of the second component preferably have a molecular weight in the range from 250 to 10,000, and are preferably polyhydroxypolyesters. Suitable polyhydroxy-polyesters (polyester-polyols) are the reaction products, which are in themselves known in polyurethane chemistry, of polycarboxylic acid, such as, for example, phthalic acid, isophthalic acid, terephthalic acid, or the dihydro, tetrahydro and hexahydro analogs thereof, such as tetrahydrophthalic acid, hexahydrophthalic acid; or alkane dicarboxylic acids having up to 8 carbon atoms, such as oxalic acid or adipic acid, with exces amount of polyhydric alcohols, such as alkane polyols, for example, alkanediols having up to 6 carbon atoms, such as ethylene glycol, propylene glycol, butanediol, hexanediol; alkanetriols having up to 6 carbon atoms, such as glycerol, trimethylolpropane, hexanetriol, trimethylolethane, and alkanetetrols having up to 6 carbon atoms such as pentaerythritol. These polyester-polyols are generally liquids of relatively high viscosity or are soft resins. It is particularly preferable to employ polyesteralcohols of phthalic acid and/or tetrahydrophthalic acid and/or hexahydrophthalic acid and trimethylolpropane and/or trimethylolethane which have a content of hydroxyl groups of from 2 to 13% by weight. Castor oil is also particularly suitable as the polyhydroxy compound. Alkyd resins of synethetic fatty acids, phthalic acids and trimethylolpropane, which have a hydroxyl content of 3.5–6% by weight, or polyacrylate or polymethacrylate containing hydroxyl groups and having a molecular weight of 1,000 to 20,000 can also be used. Polyhydroxy-polyesters which are obtained by polymerisation of ε-caprolactone and which in most cases are of low viscosity can also be used. The compounds mentioned can contain other functional groups, such as, for example, amino groups, in order to provide particular properties, such as, for example, greater reactivity.

It is necessary, when polyester-polyols with a relatively high viscosity and a large number of OH groups are used, to use reactive diluents at the same time, in order to adjust the viscosity of the fixing materials to within the above-mentioned range according to the invention. The reaction diluents are monohydric or polyhydric (e.g. dihydric, trihydric, tetrahydric, etc.) aliphatic alcohols with a molecular weight below 200, those alcohols which have a boiling point above 120° C. and a molecular weight between 45 and 200 being particularly preferred. Examples of suitable reactive diluents are alkanols, such as ethanol, pentanol, hexanol; phenyl-alkands, such as benzyl alcohol, and having up to 8 carbon atoms in the alkyl portion; alkanediols having up to 12 carbon atoms, such as ethylene glycol, propylene glycol; alkanetriols having up to 6 carbon atoms, such as trimethylolpropane, hexanetriol, glycerol; mono-esters of alkanetriols having 6 carbon atoms with alkanoic acids having up to 7 carbon atoms, such as propylene glycol monoacetate; and esters of alkanols having up to 8 carbon atoms with hydroxy-alkanoic acids having up to 6 carbon atoms, such as glycolic acid butyl ester. These reactive diluents are used in amounts of from 1 to 60, preferably 10 to 30% by weight, relative to the total amount of fixing material.

When caster oil is used as the polyhydroxy compound, it is advisable, in particular, to employ dihydric or higher polyhydric alcohols as reactive diluents.

When monoalcohols are used as reactive diluents it is, of course, necessary to ensure that the monofunctionality of the reactive diluents is compensated by the polyfunctionality of the remaining components by using trifunctional (triols) and higher polyfuntional polyesterpolyols or polyisocyanates at the same time to provide the required total amount of OH groups and the required NCO:OH ratio.

As an alternative to the use of the above-mentioned reactive diluents to lower the viscosity of the fixing materials, to the extent that this may be required, it is also possible to use oligomeric polyesters, containing at least 2 OH groups or ester-diols, with an average molecular weight of 100 to 500, preferably 200 to 500, in a concentration of 0 to 40 percent by weight, relative to the total mixture. The oligomeric polyesters containing OH groups may be prepared in accordance with the customary processes of ester formation, such as azeotropic esterification or by melt esterification. Starting components which can be employed are, for example, mixtures of diols and/or triols and dicarboxylic acids. Dicarboxylic acids which can be employed are acids which are known for the preparation of polyesters, such as phthalic acid, maleic acid, terephthalic acid and adipic acid. The molecular weight of the oligomeric polyester containing OH groups can be kept within narrow limits by adding monocarboxylic acids, such as benzoic acid, α-ethyl-hexanoic acid or hexanoic acid, to the dicarboxylic acids. Oligomeric polyesters containing OH groups can also be obtained by reacting diols with caprolactone.

The process of the disproportionating dimerisation of corresponding 3-hydroxyladehydes, such as is described in German Offenlegungsschriften (German Published Specifications) Nos. 2,500,310, 2,500,311, and 2,500,312, is suitable for the preparation of ester-diols.

In practice either or both of the use of the reactive diluents and the use of oligomeric polyesters or esterdiols may be employed to lower the viscosity of the fixing material of the invention.

The fixing materials according to the invention may also include water-absorbing or water-destroying agents, such as zeolites. Moreover, in order to adjust reactivity, catalysts which are in themselves known, such as Zn octoate or dibutyl-tin dilaurate may also be included. It is, of course, also possible to add lacquer raw materials and/or lacquer auxiliaries, such as, for example, cellulose esters, flow control agents, plasticisers, silicone oils, resins and other materials customary in the manufacture of lacquers.

Fillers, such as rock crystal or other filling materials used in dentistry may also be included.

The starting materials used in the examples which follow are the following:

PRODUCT 1

A polyester having a OH content of 8% by weight and made by standard esterification by condensing 1 mol of phthalic anhydride, 2 mols of hexahydrophthalic acid and 3.45 mols of trimethylolpropane.

PRODUCT 2

A polyester having a OH content of 7% by weight and made by standard esterification by condensing 1 moles of hexahydrophthalic anhydride and 2 mol of 2-ethyl-hexane-1,3-diol.

PRODUCT 3

A polyisocyanate, containing biuret groups, based on hexamethylene diisocyanate and having a NCO content of 22.3% by weight.

PRODUCT 4

A 50% strength paste of zeolite in caster oil (commercial product from Bayer AG, Leverkusen).

PRODUCT 5

An acrylate resin (commercial product from Monsanto Chemical Company, St. Louis).

EXAMPLE 1.

Component A

-continued

| Product 1 | 44.31 g |
|---|---|
| 2-ethylhexane-1,3-diol | 29.54 g |
| product 4 | 22.91 g |
| product 5 | 2.00 g |
| dibutyl-tin dilaurate | 0.48 g |
| zinc-II octoate | 0.76 g |
| | 100.00 g |
| Component B | |
| Product 3 | 124.17 g |

Components A and B are mixed intensively for about 60 seconds and can then be used. The pot life is about 3 minutes. After about 15 minutes, the fixing material is dry and, after 2 hours, it exhibits the hardness values indicated in the table.

EXAMPLE 2.

| Component A | |
|---|---|
| Product 1 | 40.00 g |
| Product 2 | 4.31 g |
| 2-ethylhexane-1,3-diol | 29.54 g |
| Product 4 | 22.91 g |
| Product 5 | 2.00 g |
| dibutyl-tin dilaurate | 0.48 g |
| zinc-II octoate | 0.76 g |
| | 100.00 g |
| Component B | |
| Product 3 | 120.50 g |

The processing is as in Example 1.

TABLE

| | Example 1 | | Example 2 | |
|---|---|---|---|---|
| Pendulum hardness according to DIN 53,157 [seconds] | 23° C., 50% relative humidity | 37° C., dry | 23° C., 50% relative humidity | 37° C., dry |
| After 2 hours | about 30 | about 110 | about 28 | about 100 |
| after 24 hours | about 95 | about 140 | about 92 | about 135 |
| after 7 days | about 115 | about 165 | about 105 | about 160 |
| Storage in water of the hardened samples in distilled water at 32° C., 8 days, weight loss, determined by extraction | 0 | 0 | 0 | 0 |

Crowning and bridging techniques are the main field of application for the materials according to the invention:

The stump of the tooth is rendered relatively dry after the dental technician has made the fitting to be fixed for example a metal crown. The fixing material is stirred in the prescribed mixing ratio and filled into the crown in excess. Thereafter, the crown is placed on the stump of the tooth and the patient is asked to bite on a roll of cotton wool. This fixing is continued until hardening first starts. Since about 80% of the final hardness is achieved after 2 hours, the patient can eat again after this time has elapsed.

The particular suitability as a fixing material results from the increased impact strength, the insolubility in an aqueous medium and the good adhesiveness, for example to metals.

A further field of application of the materials according to the invention is the use as a root filling material and as a sub-filling material.

When used as a root filling material, the mixed composition is introduced into the prepared root canal of a tooth, the pulp of which is dead, using a special instrument. When used as a sub-filling material, a layer is applied between the dentine and, for example, a permanent filling material. The object of this layer is to provide heat insulation and to keep any chemical interaction of the filler materials away from the pulp.

The suitability of the mixed composition as a root filling material and as a sub-filling material results from:
1. its insolubility in aqueous media;
2. the fact that the material hardens without contracting and is therefore parietal as a root filling material;
3. the homogeneous, organic barriers which are formed by the standard material;
4. the fact that the hardened material is not subjected to any extraction processes in aqueous media.

What is claimed is:

1. A two-component composition for use in forming a solvent-free fixing material suitable for use in dentistry, which fixing material is liquid at room temperature and has a viscosity in the range of from 5,000 to 100,000 cP, said composition having a first component comprising, at least one organic polyioscyanate with aliphatically and/or cycloaliphatically bonded isocyanate groups; and a second component comprising (a) at least one polyhydroxy-polyester having a molecular weight in the range of from 200 to 20,000 being substantially free of ether groups, and having at least 2 aliphatically bonded OH groups and (b) from 1 to 60% by weight, relative to the total mixture, of monohydric and/or polyhydric alcohols with a molecular weight below 200 and/or from 0 to 40% by weight, relative to the total mixture, of oligomeric polyesters containing at least 2 OH groups or ester-diols, with an average molecular weight of from 100 to 500, the first and second components of the mixture being present in amounts corresponding to a NCO/OH ratio of 1:1.

2. A composition as claimed in claim 1 wherein the organic polyisocyanate is an adduct with a viscosity of from 1,000 to 50,000 cP, of an aliphatic and/or an aromatic, diisocyanate or triisocyanate.

3. A composition as claimed in claim 1 wherein the polyisocyanate is hexamethylene diisocyanate or a derivative thereof, 1-methyl-2,4-diisocyanato-cyclohexane or 1-methyl-2,6-diisocyanato-cyclohexane or a mixture of these cyclohexane isomers, a diisocyclohexane, or 3,3,5-trimethyl-5-isocyanato-methyl-cyclohexyl isocyanate.

4. A composition as claimed in claim 1 wherein the polyhydroxy-polyester has a molecular weight of from 250 to 10,000.

5. A composition as claimed in claim 4 wherein the polyhydroxy-polyester is obtained from a polycarboxylic acid selected from phthalic acid, isophthalic acid, terephthalic acid, tetrahydrophthalic acid, hexahydrophthalic acid, oxalic acid and adipic acid, and an excess amount of a polyhydric alcohol selected from ethylene glycol, propylene glycol, butanediol, hexanediol, glycerol, trimethylolpropane, hexanetriol, trimethylolethane, pentaerythritol, and castor oil.

6. A composition as claimed in claim 1 which includes a catalyst.

7. A composition as claimed in claim 6 wherein the catalyst is Zn octoate or dibutyl-tin.

8. A composition as claimed in claim 1 which contains one or more of a pigment, lacquer and filler.

* * * * *